United States Patent

Rittinger et al.

Patent Number: 5,414,086
Date of Patent: May 9, 1995

[54] PREPARATION OF 4-METHYLPYRIMIDINES

[75] Inventors: Stefan Rittinger, Ludwigshafen; Norbert Rieber, Mannheim, both of Germany

[73] Assignee: BASF Aktiengesellschaft, Ludwigshafen, Germany

[21] Appl. No.: 199,452

[22] Filed: Feb. 22, 1994

[30] Foreign Application Priority Data

Mar. 13, 1993 [DE] Germany ............... 43 08 073.1

[51] Int. Cl.⁶ .............. C07D 239/26; C07D 239/34; C07D 239/38; C07D 239/42
[52] U.S. Cl. ..................... 544/315; 544/330; 544/242
[58] Field of Search .............. 544/315, 330, 242

[56] References Cited

PUBLICATIONS

Chem. Ber. 90, 942–952 (1957) Bredereck et al.
J. Heterocycl. Chem. 22, 1723–26 (1985) Lipinski et al.
Zh. Org. Khim. 6, 1347–1348 (1970) Moldavskii et al.
J. Heterocycl. Chem. 27, 295–305 (1990), P. Schenone et al.
Chem. Abstracts, vol. 73 (1970), Abst. No. 66528s.
Chem. Abstracts, vol. 84, (1976), Abst. No. 121763u.

*Primary Examiner*—John M. Ford
*Attorney, Agent, or Firm*—John H. Shurtleff

[57] ABSTRACT

A process for the preparation of a 4-methylpyrimidine of the general formula I

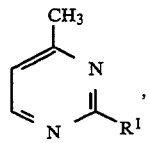

(I)

in which $R^1$ denotes $C_1$–$C_{20}$ alkyl, $C_3$–$C_8$ cycloalkyl, aryl, $C_7$–$C_{12}$ phenalkyl, $C_7$–$C_{12}$ alkylphenyl, $NH_2$, NHCN, OH, and SH, in which a 1-aminovinyl methyl ketone of the general formula II

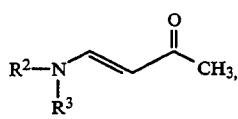

(II)

in which $R^2$ and $R^3$ denote $C_1$–$C_{20}$ alkyl, $C_3$–$C_8$ cycloalkyl, aryl, $C_7$–$C_{12}$ phenylalkyl, $C_7$–$C_{12}$ alkylphenyl, $C_1$–$C_{20}$ hydroxyalkyl or together denote a $C_2$–$C_7$ alkylene chain optionally mono- to tetra-substituted by $C_1$–$C_4$ alkyl and optionally interrupted by oxygen, nitrogen, or sulfur, is caused to react with a carboxamide or amidine or a salt thereof of the general formula III

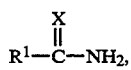

(III)

in which $R^1$ has the aforementioned meanings and x stands for oxygen or NH, at temperatures ranging from 20° to 200° C. and pressures ranging from 0.01 to 50 bar.

8 Claims, No Drawings

PREPARATION OF 4-METHYLPYRIMIDINES

The present invention relates to a process for the preparation of 4-methylpyrimidines by the reaction of 1-aminovinyl methyl ketones with acid amides.

Chem. Ber. 90, 942 to 952 (1957) and J. Heterocycl. Chem. 22, 1723-26 (1985) describe a process for the preparation of pyrimidines starting from 1,3-dicarbonyl compounds, all of which are either not available in commercial quantities or are not cheap.

Zh. Org. Khim. 6, 1347 to 1348 (1970) describes the reaction of diacetylene with guanidine derivatives to produce appropriately substituted 4-methylpyrimidines. The stated yields of 20% and the necessity to work with pure diacetylene make this process unfit for industrial use.

It is thus an object of the present invention to overcome the aforementioned drawbacks.

Accordingly, we have found a novel and improved process for the preparation of a 4-methylpyrimidine of the general fromula I

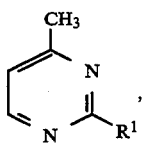    (I)

in which $R^1$ denotes $C_1-C_{20}$ alkyl, $C_3-C_8$ cycloalkyl, aryl, $C_7-C_{12}$ phenalkyl, $C_7-C_{12}$ alkylphenyl, $NH_2$, NHCN, OH, and SH,
wherein a 1-aminovinyl methyl ketone of the general formula II

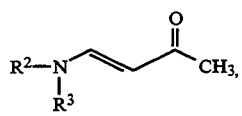    (II)

in which $R^2$ and $R^3$ denote $C_1-C_{20}$ alkyl, $C_3-C_8$ cycloalkyl, aryl, $C_7-C_{12}$ phenylalkyl, $C_7-C_{12}$ alkylphenyl, $C_1-C_{20}$ hydroxyalkyl or together denote a $C_2-C_7$ alkylene chain optionally mono- to tetra-substituted by $C_1-C_4$ alkyl and optionally interrupted by oxygen, nitrogen, or sulfur, is caused to react with a carboxamide or amidine or a salt thereof of the general formula III

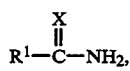    (III)

in which $R^1$ has the aforementioned meanings and x stands for oxygen or NH, at temperatures ranging from 20° to 200° C. and pressures ranging from 0.01 to 50 bar.

We have also found a novel preparation of said 1-aminovinyl methyl ketone II from diacetylene and a secondary amine by
 a) separating a partial stream, by absorption, from the cracked gas obtained in the synthesis of acetylene, which partial stream contains diacetylene of the formula IV

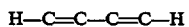    (IV), and b) causing this partial stream to react with a secondary amine of the general formula V

    (V)

in which $R^2$ and $R^3$ have the aforementioned meanings, and water, optionally in a diluent, at temperatures ranging from 0° to 150° C. and pressures ranging from 0.01 to 5 bar.

The process of the invention can be carried out as follows:

The 1-aminovinyl methyl ketone II and the carboxamide III can be placed in a vessel optionally in an inert solvent and the carboxamide III is added under controlled temperature conditions.

The reaction can be carried out optionally in the presence of from 0.001 to 1000 wt % and preferably from 0.005 to 500 wt % and more preferably from 0.01 to 200 wt % of an acid or base acting as catalyst at temperatures of from 20° to 200° C. and preferably from 40° to 180° C. and more preferably from 50° to 160° C. and pressures of from 0.01 to 50bar and preferably from 0.1 to 5 bar and more preferably at atmospheric pressure (standard pressure) batchwise or, preferably, continuously in the gas phase or, preferably, in the liquid phase. Advantageously, the resultant water of reaction can be removed from the circuit using conventional entraining agents.

Suitable inert solvents are formamides, for example, dialkyl formamides such as dimethylformamide, lactams such as N-methylpyrrolidone, alcohols, for example, $C_1-C_{20}$ alkanols such as methanol and ethanol, aromatic hydrocarbons, for example, $C_7-C_{20}$ alkylaryls such as benzene, toluene, o-xylene, m-xylene, p-xylene, xylene isomer mixtures and preferably mixtures of aromatics, eg the mixtures of aromatics usually formed when cracking hydrocarbons (residual oils), or glycol ethers such as ethylene glycol diethyl ether for example.

Examples of suitable acids are mineral acids such as hydrochloric acid, sulfuric acid, nitric acid, phosphoric acid, sulfonic acids such as methanesulfonic acid, and p-toluenesulfonic acid.

Suitable bases are inorganic bases, for example, hydroxides such as sodium hydroxide, potassium hydroxide, and calcium hydroxide or organic bases, for example, ammonia, primary, secondary and tertiary amines, alcoholares, for example, $C_1-C_8$ alkali-metal alcoholares and $C_1-C_8$ alkaline earth metal alcoholares such as sodium methanolate, pyridine and imidazoles.

The present process is suitable in particular for utilizing diacetylene-containing partial streams. The mixture of higher acetylenes occurring as a dilute partial stream on separation of cracked gases coming from a plant for cracking hydrocarbons under acetylene synthesis conditions can usually be directly reacted, without further physical or chemical treatment, with aqueous solutions of secondary amines at temperatures ranging from 0° to 150° C. and preferably from 30° to 130° and more preferably from 40° to 120° C. and pressures of from 0.01 to 5 bar and preferably from 0.1 to 2.5 bar and more preferably from 0.5 to 1.5 bar, at standard pressure (atmospheric pressure).

The technical modifications to the production and treatment of the cracked gases used in the present invention are described, for example, in *Ullmanns Encyclopedia of Industrial Chemistry*, 5th Edition, A1, 1985, pp. 97 to 145, in particular p. 111, FIG. 13, according to which hydrocarbons (for example, natural gas or higher-boiling fractions) are cracked at the high temperatures necessary for the formation of acetylene and the resulting products are quenched directly downstream of the reaction zone (cracking zone) by treatment with a jet of liquid (for example, water or oil). The composition of the cracked gases is dependent on the starting materials used for the cracking operation as well as on the cracking conditions.

The partial streams used in the present invention are produced during separation of the cracked gas by a series of physical separating operations and preferably by combined absorption/desorption processes in a series of washing and stripping circuits, in a number of partial streams. The useful partial streams containing higher acetylenes have concentrations of diacetylene which are distinctly higher than in the cracked gas.

Further treatment of the stream used as required in DE-A 2,157,537 is unnecessary. Both liquid streams and gaseous partial streams obtained by stripping (desorption) of the washings are characterized by a distribution profile of the higher acetylenes which, compared with the cracked gas, are more conducive to the desired conversion to aminovinyl methyl ketone. Only unsubstantial amounts of other higher acetylenes are present, (pentadiyne, hexadiyne, etc) since these are previously separated. This leads to high purity of the resulting product.

Diacetylene-containing hydrocarbon condensates (the so-called BTX fraction) from this gas stream are equally well suited for the said conversion of diacetylene to 1-aminovinyl methyl ketone. This has an added advantage for the operating procedure in that when the reaction of diacetylene is complete the BTX fraction can be obtained—freed from diacetylene—by distillation, and this can be reused as starting material for cracking, for example.

Suitable absorbents for use in processing cracked gases are water, high-boiling hydrocarbons such as mixtures of aromatics, preferably residual oil, N-alkyl lactams containing $C_1$-$C_3$ alkyl, preferably N-methylpyrrolidone, $C_1$-$C_5$ alcohols, preferably methanol, acid amides, preferably dimethylformamide, alkylated cyclic ureas, preferably dimethylpropylene urea, primary, secondary and tertiary $C_1$-$C_6$ amines, and ammonia.

Dilution of the diacetylene-containing gases removed from the absorbent is suitably effected using inert gases such as hydrocarbons, carbon monoxide, synthesis gas, lean gas, and nitrogen, or mixtures of these gases, and preferably natural gas and/or acetylene.

The gas mixture which has been rendered inert usually contains, preferably, from 55 to 85 vol % of inert gas, from 1 to 30 vol % of diacetylene, and from 10 to 20 vol % of other components such as acetylene, vinylacetylene, and benzene. The concentration of diacetylene in the gas mixture which has been rendered inert is usually from 1 to 30 vol % and preferably from 5 to 20 vol %. The upper limit is determined by the limit of spontaneous explosive decomposition in the inert gas.

Typical gaseous partial streams containing higher acetylenes have the following composition:
58 vol % of methane, 18 vol % of diacetylene, 5 vol % of nitrogen, 4 vol % of acetylene, 4.5 vol % of vinylacetylene, 4 vol % of benzene, 2vol % of ethane, 2 vol % of cyclopentadiene, 2.5 vol % of residual components.

Typical liquid partial streams containing higher acetylenes have the following composition:
32vol % of benzene, 28vol % of toluene, 17 vol % of xylene (BTX), 8 vol % of styrene, 6 vol % of diacetylene, methanol (89 vol %), acetylene (0.6 vol %), diacetylene (2.2 vol %), vinylacetylene (0.4 vol %), cyclopentadiene (1 vol %), benzene (1.8 vol %) and toluene (1.3 vol %).

The reaction of the partial stream with aqueous secondary amines may be carried out continuously or batchwise. When using a gaseous partial stream processes are advantageous which achieve good gas distribution in liquids, for example, which involve equipment such as a gassing ring, a perforated plate, compressive liquid/gas mixing means, a spray reactor or an absorber tower.

Any unconverted amine can be separated by distillation of the product or the product directly obtained therefrom on further processing and then recycled to synthesis stage a).

The gas mixture flowing from a plant for working up cracked gases usually comes with a temperature slightly above ambient. A preliminary separation of readily condensable gaseous components in separating vessels disposed in the reactor inlet line, at ambient temperature, improves the purity of the crude product.

The substituents $R^1$, $R^2$, $R^3$ and x in the compounds of formulas I, II, III, and V have the following meanings: individually, $R^1$, $R^2$, and $R^3$ can denote:

$C_1$-$C_{20}$ alkyl and preferably $C_1$-$C_8$ alkyl and more preferably $C_1$-$C_4$ alkyl such as methyl, ethyl, n-propyl, isopropyl, n-butyl, isobutyl, sec-butyl and tert-butyl, $C_3$-$C_8$ cycloalkyl and preferably $C_5$-$C_8$ cycloalkyl such as cyclopentyl, cyclohexyl, cycloheptyl, and cyclooctyl and more preferably cyclopentyl and cyclohexyl, aryl such as phenyl, 1-naphthyl, and 2-naphthyl and preferably phenyl, 1-naphthyl, and 2-naphthyl and more preferably phenyl, $C_7$-$C_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,5-dimethylphenyl, and 2,3,4-trimethylphenyl, $C_7$-$C_{12}$ phenylalkyl such as benzyl, 1-phenethyl, 2-phenethyl, 1-phenylpropyl, 2-phenylpropyl, 1-phenylbutyl, 2-phenylbutyl, and 3-phenylbutyl and preferably benzyl, 1-phenethyl, and 2-phenethyl, and, in addition, $R^1$ can denote $NH_2$, NHCN, OH, and SH and $R^2$ and $R^3$ can individually denote $C_1$-$C_{20}$ hydroxyalkyl and preferably $C_2$-$C_8$ hydroxyalkyl and more preferably $C_2$-$C_4$ hydroxyalkyl such as 2-hydroxyethyl and 3-hydroxypropyl, or together they can denote:

a $C_2$-$C_7$ alkylene chain optionally substituted by from one to four $C_1$-$C_4$ alkyl radicals and optionally interrupted by oxygen, nitrogen, or sulfur, such as —$(CH_2)_2$—, —$(CH_2)_3$—, —$(CH_2)_4$—, —$(CH_2)_5$—, —$(CH_2)_6$—, —$(CH_2)_7$—, —$(CHCH_3)$—, —$(CH_2)$—O—$(CH_2)_2$—, —$(CH_2)_2$—N—$(CH_2)_2$—, and —$(CH_2)_2$—S—$(CH_2)_2$— and x denotes oxygen or NH.

The 4-methylpyrimidines I are starting products for the preparation of biologically active substances (DE-A 816,700; U.S. Pat. No. 2,725,384; DE-A 871,303; U.S. Pat. No. 2,688,015, U.S. Pat. No. 2,690,439 and U.S. Pat. No. 2,690,466; WO-A 92/10,490).

EXAMPLES

In the following examples, the diacetylene-containing gas mixture which has been rendered inert is referred to as HA gas. The diacetylene in the HA gas or in the exhaust gas following the reaction was analyzed by gas chromatography on a packed column (20% Reoplex 400 on Chromosorb PAW) using $N_2$ as carrier gas (35 mL/min.) and an FID detector. The concentrations are given as percentages by volume.

EXAMPLE 1

A mixture of 67 g of morpholine and 33 g of $H_2O$ was placed in a stirred vessel having a capacity of 500 mL, and heated to 80° C. 15 L/h of a partial stream of exhaust HA gas coming from an acetylene synthesis plant were passed through the reaction solution via an inlet pipe equipped with a glass frit over an operating period of 12 h. The diacetylene concentration of the HA gas at the reactor inlet varied from 4 to 9%. With the average depletion of the diacetylene being greater than 90%, 130 g of dark colored reaction solution containing residual morpholine in a concentration of 18% and 1-morpholinovinyl methyl ketone in a concentration of 60% were obtained. Following installation of a distillation bridge, a mixture of water and morpholine was removed by distillation at ca 200 mbar/75° C. Residual amine was removed by reducing the pressure to 20 mbar. The dark brown colored residues contained 1-morpholinovinyl methyl ketone in a concentration of 90% (85 g).

EXAMPLE 2

85 g of enamine ketone from Example 1 were diluted with 500 mL of xylene (at a purity of 90% equivalent to 0.5 mol) in a stirred glass flask having a capacity of 1 L. 0.5 mol (90 g) of guanidinium carbonate was added to the solution and the mixture was then refluxed with stirring at the water circulator. After a period of 60 h, no more enamine ketone was detectable by GC analysis. The removal of the water of reaction was also quantitative (0.5 mol=9 g). The contents of the reactor were filtered. There were obtained from the flitrate, after removal, by distillation, of the solvent, 45.2 g (75%) of 2-amino-4-methyl pyrimidine (mp 160°–162° C.) in the form of colorless crystals.

EXAMPLE 3

A mixture of 5.4 g of sodium methanolate, 9.5 g of acetamidinium chloride, and 17.2 g of 90% strength enamine ketone from Example 1 (each 0.1 mol) in 200 mL of ethanol was fed to stirred apparatus having a capacity of 500 mL. Refluxing was carried out over a period of 3 h, after which the enamine ketone was found to have undergone quantitative conversion and the initially brown suspension had become almost colorless (pale yellow). The reaction solution was distinguishable by an unpleasant, pyridine-like odor. 2,4-Dimethyl pyrimidine could be identified by gas chromatography by injecting an authentic sample. The content thereof in the reaction solution (6 percent by area) indicated a yield of 80%.

We claim:

1. A process for the preparation of a 4-methylpyrimidine of the formula

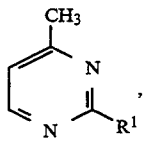

in which $R^1$ is $C_1$–$C_{20}$-alkyl, $C_3$–$C_8$-cycloalkyl, phenyl, naphthyl, $C_7$–$C_{12}$-phenalkyl, $C_7$–$C_{12}$-alkylphenyl, $NH_2$, NHCN, OH or SH, which comprises reacting a 1-aminovinyl methyl ketone of the formula

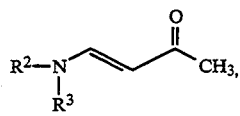

in which each of $R^2$ and $R^3$, when taken individually, is $C_1$–$C_{20}$-alkyl, $C_3$–$C_8$-cycloalkyl, phenyl, naphthyl, $C_7$–$C_{12}$-phenalkyl, or $C_7$–$C_{12}$-alkylphenyl, or in which $R^2$ and $R^3$, when taken together form a $C_2$–$C_7$-alkylene chain optionally mono- to tetra-substituted by $C_1$–$C_4$-alkyl and optionally interrupted by a single oxygen, nitrogen or sulfur atom, with a carboxamide or amidine, including a salt thereof, of the formula

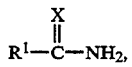

in which $R^1$ has the aforementioned meanings and X is oxygen or NH, at a temperature of from 20° to 200° C. and a pressure of from 0.01 to 50 bar.

2. A process for the preparation of a 4-methylpyrimidine I as claimed in claim 1, wherein the reaction is carried out at temperatures ranging from 40° to 180° C.

3. A process as claimed in claim 1, wherein the reaction is carried out at a temperature of from 50° to 160° C.

4. A process as claimed in claim 1, wherein the reaction is carried out at a pressure of from 0.1 to 5 bar.

5. A process as claimed in claim 1, wherein the reaction is carried out under atmospheric pressure.

6. A process as claimed in claim 1, wherein the reaction is carried out in the presence of a water immiscible organic solvent and water of reaction is removed from the reaction mixture.

7. A process as claimed in claim 1, wherein a salt of the compound III is reacted with the ketone II in an inert polar solvent and in the presence of a basic compound.

8. A process as claimed in claim 1, wherein $R^2$ and $R^3$ of the ketone II, when taken together with the nitrogen atom to which they are attached, form a 6-membered heterocyclic ring and are selected from the group consisting of —(CH$_2$)$_5$—, —(CH$_2$)$_2$—O—(CH$_2$)$_2$—, —(CH$_2$)$_2$—N—(CH$_2$)$_2$— and —(CH$_2$)$_2$—S—(CH$_2$)$_2$—.

* * * * *